US006780842B2

(12) United States Patent
Paquin et al.

(10) Patent No.: US 6,780,842 B2
(45) Date of Patent: Aug. 24, 2004

(54) CERULOPLASMIN AND AN ANTIOXIDANT COMPOSITION COMPRISING THE SAME AND THEIR USES AS NEUROPROTECTIVE AGENT

(75) Inventors: Joanne Paquin, Montréal (CA); Mircea-Alexandru Mateescu, Montréal (CA); Éric De Grandpré, Joliette (CA)

(73) Assignee: Warner-Lambert Company LLC, Morris Plains, NJ (US)

(*) Notice: Subject to any disclaimer, the term of this patent is extended or adjusted under 35 U.S.C. 154(b) by 0 days.

(21) Appl. No.: 10/012,730

(22) Filed: Nov. 5, 2001

(65) Prior Publication Data

US 2002/0094949 A1 Jul. 18, 2002

Related U.S. Application Data

(63) Continuation of application No. PCT/CA00/00529, filed on May 5, 2000.

(30) Foreign Application Priority Data

May 5, 1999 (CA) .............................................. 2270853

(51) Int. Cl.$^7$ ........................ A61K 38/00; C07K 14/00; C07K 17/00
(52) U.S. Cl. ............................ 514/2; 530/350; 530/380
(58) Field of Search ................................ 530/350, 380, 530/300; 514/2, 6, 547, 557, 560, 458, 725

(56) References Cited

U.S. PATENT DOCUMENTS

| | | | | |
|---|---|---|---|---|
| 5,395,822 A | | 3/1995 | Izumi et al. .................... | 514/3 |
| 2002/0128316 A1 | * | 9/2002 | Paquin et al. | |

FOREIGN PATENT DOCUMENTS

| | | | | |
|---|---|---|---|---|
| WO | 93/16690 | 9/1993 | .......... | A61K/31/19 |
| WO | 95/28956 | 11/1995 | .......... | A61K/38/57 |
| WO | 98/25954 | 6/1998 | ........... | C07K/14/00 |

OTHER PUBLICATIONS

Wells (Sep. 18, 1990) "Additivity of Mutational Effects in Proteins." Biochemistry 29(37): 8509–8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492–495.*
Bork (2000) "Powers and Pitfalls in Sequence Analysis: The 70% Hurdle." Genome Research 10:398–400.*
Skoinick and Fetrow (2000) "From gene to protein structure and function: novel applications of computational approaches in th genomic era." Trends in Biotech. 18(1): 34–39.*
Doerks et al., (Jun. 1998) "Protein annotation: detective work for function prediction." Trends in Genetics 14(6): 248–250.*
Smith and Zhang (Nov. 1997) "The challenges of genome sequence annotation or 'The devil is in the details'." Nature Biotechnology 15: 1222–1223.*
Brenner (Apr. 1999) "Errors in genome annotation." Trends in Genetics 15(4): 132–133.*
Bork and Bairoch (Oct. 1996) "Go hunting in sequence databases but watch out for the traps." Trends in Genetics 12(10): 425–427.*
Harris et al. (Mar. 1995) "Aceruloplasminemia: Molecular characterization of this disorder of iron metabolism." PNAS 92: 253 2543.*
Samokyszyn et al. (Jan. 5, 1989) "Inhibition of Superoxide and Ferritin–dependent Lipid Peroxidation by Ceruloplasmin." The Journal of Biological Chemistry 264(1): 21–26.*
Daimon et al. (Jul. 2000) "A Novel Mutation of the Ceruloplasmin Gene in a Patient with Heteroallelic Ceruloplasmin Gene Mutation (HypoCPGM)." Tohoku J. Exp. Med. 191(3): 119–125.*
Wang et al. (Feb. 15, 1995) "Ceruloplasmin: An Endogenous Depolarizing Factor in Neurons?" Biochemical and Biophysica Research Communications 207(2): 599–605.*
Chahine et al. (Oct. 1991) "Protective effects of ceruloplasmin against electrolysis–induced oxygen radicals in rat heart." Can. J. Physiol. Pharmacol. 69(10): 1459–1464.*
Bharatkumar N. Patel et al., "A Novel Glycosylphosphatidylinositol–Anchored Form of Ceruloplasmin is Expressed by Mammalian Astrocytes", The Journal of Biological Chemistry, vol. 272, No. 32, Issue of Aug. 8, pp. 20185–20190 (1997), XP–002063796.
English abstract of RU2136274 (Knyazkova L G; Suverneva L Al; and, Tsvetovskaya G A; RU 19960114547; Jul. 22, 1996).

* cited by examiner

Primary Examiner—Elizabeth Kemmerer
Assistant Examiner—Christopher James Nichols
(74) Attorney, Agent, or Firm—Barry H. Jacobsen; Evan J. Federman

(57) ABSTRACT

A neuroprotective composition for protecting neuronal cells against oxidative stress and methods for using and preparing the same. More particularly, the neuroprotective composition of the invention comprises a therapeutically effective amount of ceruloplasmin or a functional derivative thereof. The neuroprotective composition is characterized in that it protects neuronal cells from reactive oxygen species such as •$O_2^-$ and •OH. In a preferred embodiment, the neuroprotective composition further comprises an antioxidant consisting of catalase or of an amphiphilic physiological antioxidative solution comprising a mixture of pyruvate, antioxidant, and lipid(s) such as fatty acids. The neuroprotective composition could be used for the treatment of brain trauma, brain or cerebrovascular ischemia, neurodegenerative diseases, poisoning of neuronal cells, the diminution of drugs side effects and for preservation of neuronal grafts.

12 Claims, 4 Drawing Sheets

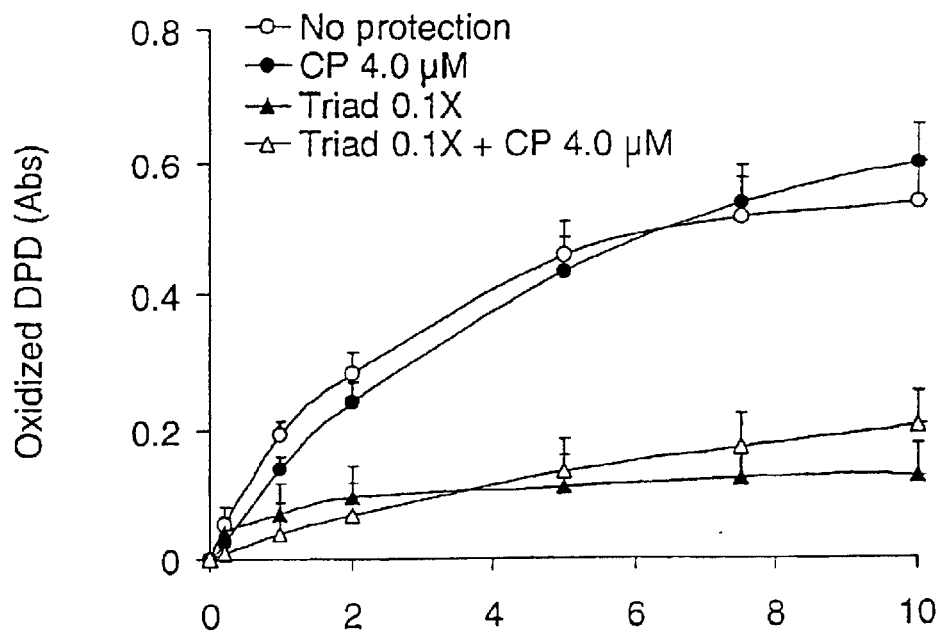
FIG. 5   Hydrogen peroxide concentration (mM)
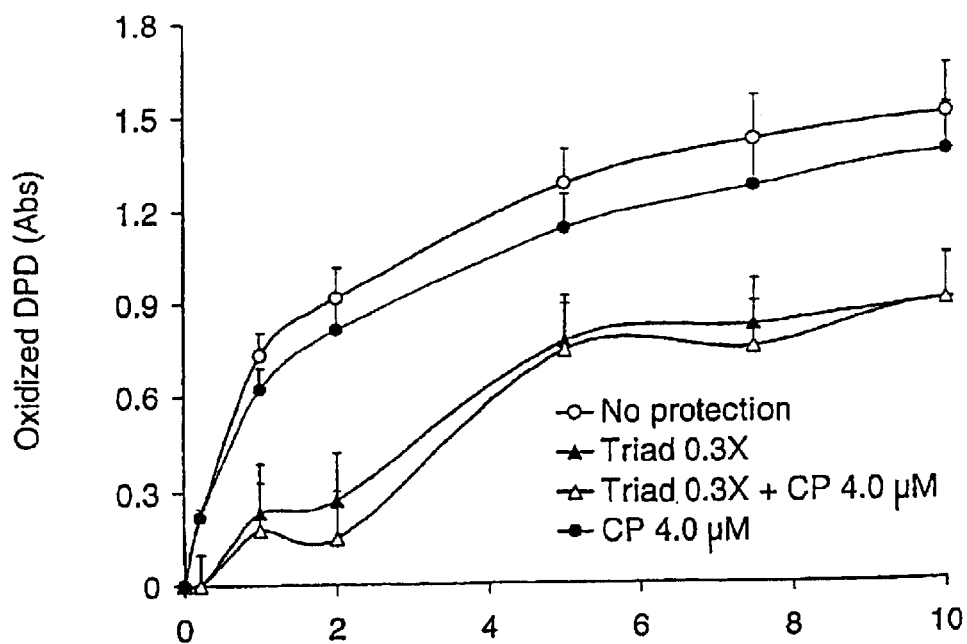
FIG. 6   Hydrogen peroxide concentration (mM)

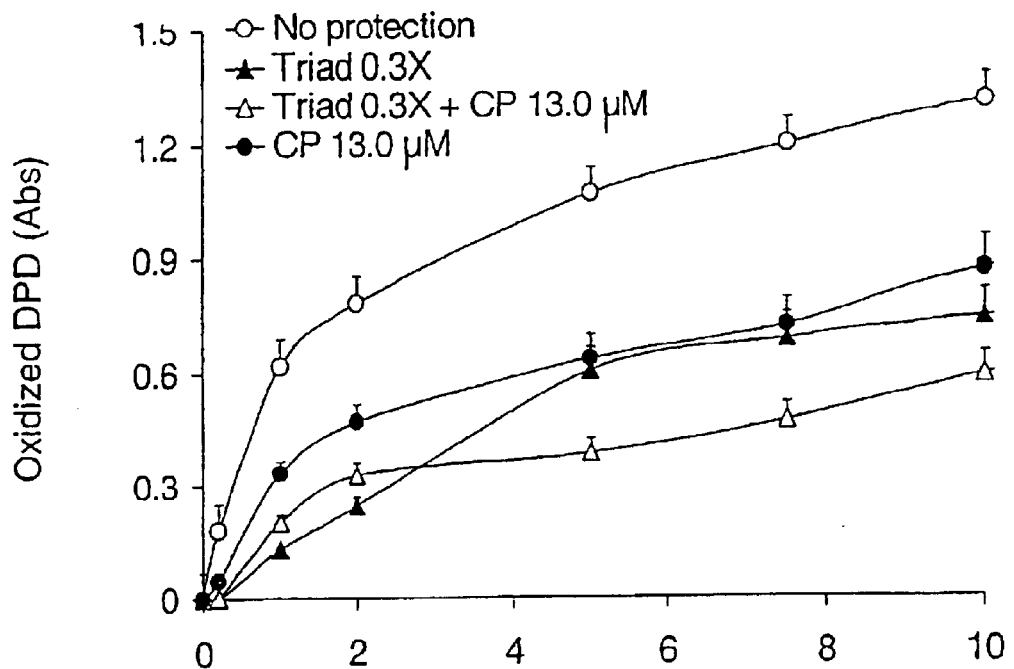
FIG. 7    Hydrogen peroxide concentration (mM)
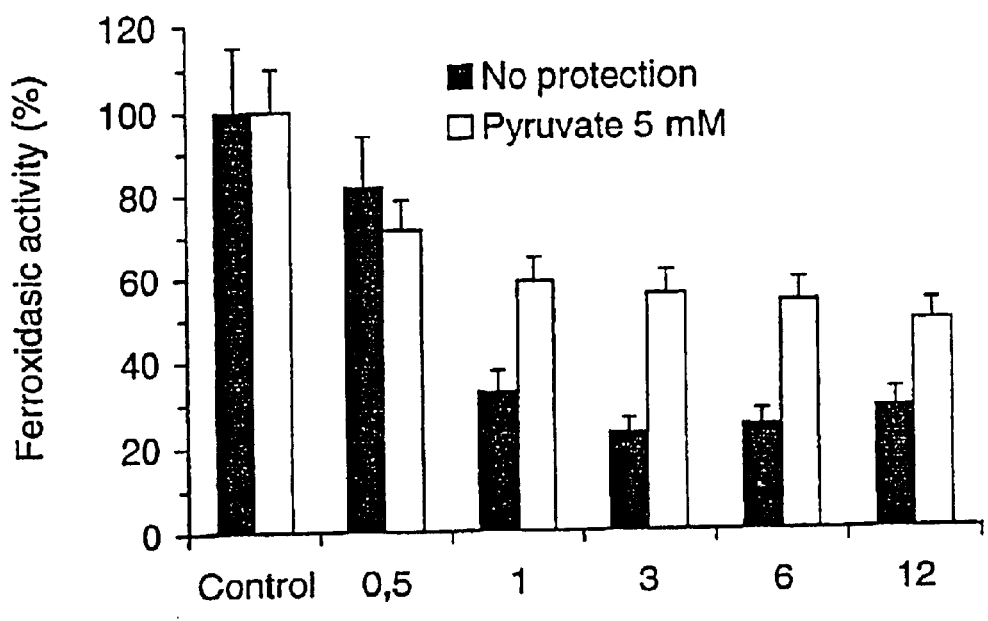
FIG. 8    Time (hours)

CERULOPLASMIN AND AN ANTIOXIDANT COMPOSITION COMPRISING THE SAME AND THEIR USES AS NEUROPROTECTIVE AGENT

This is a continuation of international application Serial No. PCT/CA00/00529, filed May 5, 2000, the entire disclosure of which is hereby incorporated by reference.

BACKGROUND OF THE INVENTION

1. Field of the Invention

The present invention relates to the use of ceruloplasmin (and/or derivatives thereof) in a neuroprotective composition. Preferably, the composition of the invention comprises ceruloplasmin and a combination of pyruvate, antioxidant, lipid(s) such as fatty acids since these four components were found to synergistically protect neurons against oxidative stress.

2. Description of the Prior Art

Reactive oxygen species (ROS) have been implicated in the development of many heart and brain dysfunctions. Ischemia/reperfusion insults to these organs are among the leading causes of mortality in America. These insults are caused by complete or partial local occlusions of heart and brain vasculature, by heart stroke or attack, and by cerebral attacks and trauma to the brain. In addition, ROS are involved in artherosclerotic lesions, in the evolution of various neurodegenerative diseases, and are also produced in association to epileptic episodes, in inflammation, in the mechanisms of action of various neurotoxicants, or as side-effects of drugs.

Until now, no ideal therapeutic agent was known to protect neuronal cells against oxidant species associated with various types of oxidative stress. It would therefore be highly desirable to have such neuroprotective agent.

TRIAD is combination of pyruvate, antioxidant and fatty acids. This composition has been patented in 1997 in the U.S. as a therapeutic wound healing compositions (U.S. Pat. No. 5,652,274). Many related U.S. patents have also been issued for covering the uses of TRIAD in antikeratolytic compositions (U.S. Pat. No. 5,641,814); in anti-fungal compositions (U.S. Pat. No. 5,663,208); in acne healing compositions (U.S. Pat. No. 5,646,190); in anti-inflammatory compositions (U.S. Pat. No. 5,648,380); in dermatological compositions (U.S. Pat. No. 5,602,183); in sunscreen compositions (U.S. Pat. No. 5,674,912); in antihistamine compositions (U.S. Pat. No. 5,614,561); in cytoprotective compositions (U.S. Pat. No. 5,633,285); in wound healing composition affixed to razor cartridges (U.S. Pat. No. 5,682,302); and in regenerating compositions (EP 0 573 465 B1). However, none of these patents discloses or suggests the use of TRIAD as neuroprotective agent.

Ceruloplasmin (CP), is a multifunctional blue-copper plasma protein which has important antioxidant and free radical scavenging properties as well as a ferroxidase I activity. Ceruloplasmin was also shown as an important oxygen free radical (OFR) scavenger. Recent studies related to the alterations in the level of ceruloplasmin further support a dominant role of this protein, suggesting possible therapeutic applications. For example, international patent application No WO9825954 relates to the use of modified ceruloplasmin comprising a glycosylphosphatidylinositol moiety and its use for the treatment of toxic level of ferrous iron. Although the ROS scavenging capacities of CP has been shown in vitro, none of these studies has suggested the use of CP as neuroprotective agent neither they have shown that CP was sensitive in this action to the presence of selected antioxidants. These studies have not demonstrated or suggested either that CP could have a synergic neuroprotective action against oxidative stress when used in combination with a formulation of pyruvate, antioxidant and fatty acids. These discoveries were therefore unexpected and open the field of more powerful therapeutic applications to these known compounds.

In view of the above, it is clear that there is a need for neuroprotective compositions comprising ceruloplasmin (and/or derivatives thereof). There is also a need for anti-oxidative neuroprotective compositions comprising ceruloplasmin, pyruvate, antioxidant(s), lipid(s) such as fatty acid since these four components synergistically enhance their respective neuroprotective effects against oxidative stress, as it will be shown herein after.

The purpose of this invention is to fulfil these needs along with other needs that will be apparent to those skilled in the art upon reading the following specification.

SUMMARY OF THE INVENTION

The present invention relates to a neuroprotective composition and more particularly to a composition comprising ceruloplasmin and its uses.

According to an aspect of the invention, the neuroprotective composition comprises a therapeutically effective amount of ceruloplasmin or a functional derivative thereof. It is characterized in that it protects neuronal cells from reactive oxygen species such as $\bullet O_2^-$ and $\bullet OH$. Advantageously, ceruloplasmin or its functional derivative is purified from blood using an one-step affinity chromatography on aminoethyl-agarose.

According to another aspect of the invention, the neuroprotective composition further comprises an antioxidant consisting of: i) catalase; and/or ii) an amphiphilic physiological antioxidative solution, ceruloplasmin or the functional derivative of ceruloplasmin and the antioxidant being present in an amount that have a synergistic beneficial effect on neuronal cells. In a preferred embodiment, the amphiphilic physiological antioxidative solution comprises a mixture of pyruvate, at least one antioxidant and at least one lipid.

In a preferred embodiment, lipids consist of a mixture of saturated and unsaturated fatty acids selected from the group consisting of monogylcerides, digylcerides, trigylcerides, free fatty acids, and mixtures thereof.

Preferably, pyruvate is selected from the group consisting of pyruvic acid, pharmaceutically acceptable salts of pyruvic acid, prodrugs of pyruvic acid, and mixtures thereof.

Preferably, also the antioxidant is selected from lipid-soluble antioxidants, and more preferably the antioxidant is selected from the group consisting of Vitamin A, carotene, Vitamin E, pharmaceutically acceptable salts thereof, and mixtures thereof.

According to an other aspect of the invention, the neuroprotective composition is used as such or as an active agent in the preparation of a medication for the treatment of neuronal cells. Such treatments include the treatment brain trauma, brain or cerebrovascular ischemia, neurodegenerative diseases, poisoning of neuronal cells, the diminution of drugs side effects and for preservation of neuronal grafts.

According to an other aspect of the invention, the invention provides a method for treating neuronal oxidative stress related condition, the method comprising administrating to a patient in need thereof i) a therapeutically effective amount of ceruloplasmin or a functional derivative thereof; or ii) component i) in combination with catalase or in combination with a mixture of pyruvate, at least one antioxidant and at least one lipid.

Alternatively, the invention also provides a method for treating neuronal oxidative stress related condition comprising: a) administrating to a patient in need thereof, a therapeutically effective amount of an antioxidative composition comprising ceruloplasmin or a functional derivative thereof, pyruvate and at least one antioxidant; and b) providing, into the blood circulation of this patient, at least one lipid having a synergistic therapeutic effect on neuronal cells in combination with said antioxidative composition. The lipid(s) could be provided to the patient by increasing its lipidic blood level ratio through its diet. Examples of neuronal oxidative stress related condition include a neurodegenerative disease, such as amyotrophic lateral sclerosis, Alzheimer's disease, Parkinson's disease Huntington's disease, etc, brain trauma, brain or cerebrovascular ischemia, neuronal cells poisoning, side effects caused by a drug and the preservation of neuronal grafts.

According to an other aspect of the invention it is provided a method for preparing a neuroprotective composition, the method comprising the steps of:

a) providing a therapeutically effective amount of i) ceruloplasmin or a functional derivative of ceruloplasmin, ii) pyruvate, iii) at least one antioxidant and iv) at least one lipid; and b) mixing together components i), ii), iii) and iv) of step a) in a buffered saline solution to obtain a pharmaceutically acceptable homologous suspension; and optionally c) centrifuging or filtering the homologous suspension obtained in step b).

The buffered saline solution may comprises sodium, potassium, magnesium and calcium ions at physiological concentrations and if necessary, an emulsifier.

An advantage of the present invention is that it provides effective means for maintaining or stimulating the capacity of neuronal cells to maintain or recover their viability or function in conditions of oxidative stress. It can also protect neuronal cells from a toxic substance or a stress, stabilizes the cellular membrane of a neuronal cell and/or helps in the normalization of neuronal cellular functions.

Other objects and advantages of the present invention will be apparent upon reading the following non-restrictive description of several preferred embodiments made with reference to the accompanying drawings.

DESCRIPTION OF THE DRAWINGS

FIG. 5 is a graph showing the in vitro antioxidant capacity of CP and TRIAD, in the conditions of $H_2O_2$ prooxidant system used with P19 neurons.

FIG. 6 is a graph showing the in vitro antioxidant capacity of CP 4 $\mu$M and TRIAD in the conditions of $H_2O_2/Fe^{2+}$ prooxidant system.

FIG. 7 is a graph showing the in vitro antioxidant capacity of CP 13 $\mu$M and TRIAD in the conditions of $H_2O_2/Fe^{2+}$ prooxidant system. of CP ferroxidase activity by pyruvate in vitro.

FIG. 8 is a graph showing the protection of CP ferroxidase activity by pyruvate in vitro.

DETAILED DESCRIPTION OF THE INVENTION

Figure 1:
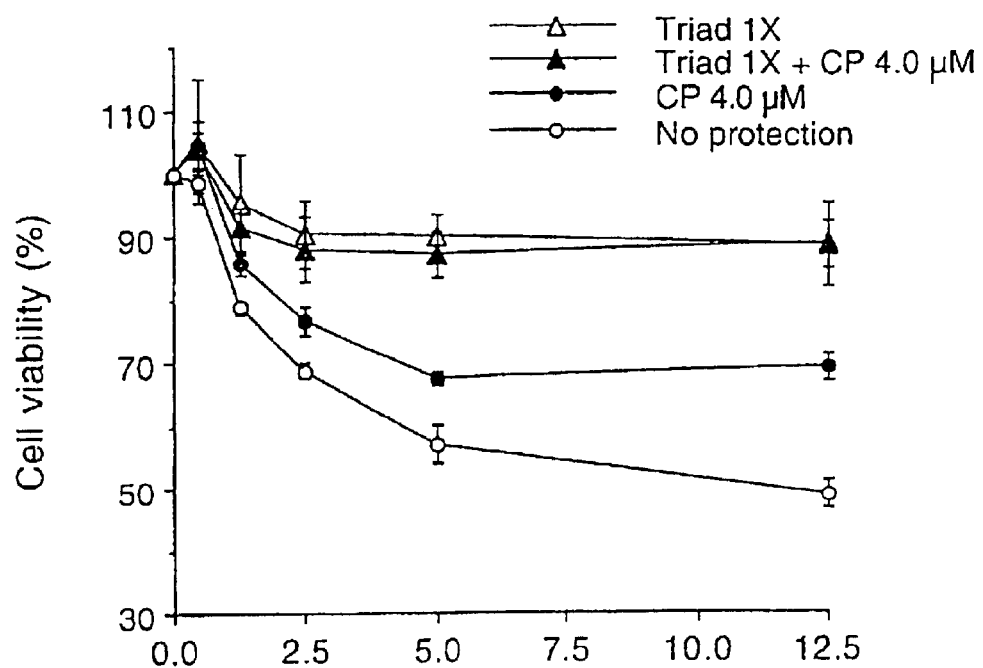
FIG. 1 is a graph showing the protection provided by CP and TRIAD to P19 neurons exposed to mild oxidative stress conditions mediated by XA/XAO.

As stated hereinbefore the present invention relates to the use of ceruloplasmin alone or in combination with antioxidant(s) and its use in a neuroprotective composition. The Inventors have discovered that compositions comprising ceruloplasmin have neuroprotective actions against oxidative stress. It has also been found that the neuroprotective action of ceruloplasmin was even more important when ceruloplasmin was combined with antioxidants and more particularly with an amphiphilic physiological antioxidative solution comprising pyruvate, an antioxidant (such as Vitamin E), and lipid(s) such as fatty acids. Indeed, these four components synergistically protect neurons against oxidative stress.

Unless defined otherwise, all technical and scientific terms used herein have the same meaning as commonly understood by one ordinary skilled in the art to which this invention belongs.

As used herein, the term "neuroprotective agent" or "neuroprotective composition" refers to any compound (or to any mixture of compounds) that protects a neuronal cell from the loss of viability or function induced by a toxic substance, stabilizes the cell membrane of a neuronal cell and/or helps in the normalization of neuronal cell functions.

Therefore, the term "neuroprotection" as used herein refers to the capacity of a neuroprotective agent to maintain or stimulate the capacity of neuronal cells to maintain or recover their neuronal functions even in pathological or harmful conditions such as oxidative stress conditions.

As stated previously, ceruloplasmin (CP), is a multifunctional blue-copper plasma protein whose most known function is the copper transport. Ceruloplasmin also has important antioxidant and free radical scavenging properties as well as a ferroxidase I activity. Another important role has recently been postulated for this protein as a regulator of iron metabolism.

The ceruloplasmin useful according to the present invention comprises substantially pure ceruloplasmin generally purified from blood or produced by recombinant techniques and functional derivatives thereof. As generally understood and used herein, the term substantially pure refers to a ceruloplasmin preparation that is generally lacking in other cellular or blood components.

A "functional derivative", as is generally understood and used herein, refers to a protein sequence that possesses a functional biological activity that is substantially similar to the biological activity of the whole protein sequence. A functional derivative of a protein may or may not contain post-translational modifications such as covalently linked carbohydrate, if such modification is not necessary for the performance of a specific function. The term "functional derivative" is intended to the "fragments", "segments", "variants", "analogs" or "chemical derivatives" of a protein.

The terms "fragment" and "segment" as is generally understood and used herein, refer to a section of a protein, and are meant to refer to any portion of the amino acid sequence.

The term "variant" as is generally understood and used herein, refers to a protein that is substantially similar in structure and biological activity to either the protein or fragment thereof. Thus two proteins are considered variants if they possess a common activity and may substitute each other, even if the amino acid sequence, the secondary, tertiary, or quaternary structure of one of the proteins is not identical to that found in the other.

The term "analog" as is generally understood and used herein, refers to a protein that is substantially similar in function to ceruloplasmin.

As use herein, a protein is said to be a "chemical derivative" of another protein when it contains additional chemical moieties not normally part of the protein, said moieties being added by using techniques well know in the art. Such moieties may improve the protein's solubility, absorption, bioavailability, biological half life, and the like. Any undesirable toxicity and side-effects of the protein may be attenuated and even eliminated by using such moieties. For example, CP and CP fragments can be covalently coupled to biocompatible polymers (polyvinyl-alcohol, polyethyleneglycol, etc) in order to improve stability or to decrease antigenicity. They could also be coupled to proteins (or their chemical derivatives) known to pass the blood-brain barrier via transcytosis across vascular endothelial cells (e.g. transferrin).

The amount of ceruloplasmin and/or functional derivatives thereof present in the neuroprotective composition of the present invention is a therapeutically effective amount. A therapeutically effective amount of ceruloplasmin is that amount of ceruloplasmin or derivative thereof necessary to prevent and/or reduce injury of a neuronal mammalian cell. Preferably, the amount of ceruloplasmin in the composition is such that ceruloplasmin can synergistically, in combination with the other components of the composition, prevent and/or reduce injury of a neuronal mammalian cell. The exact amount of ceruloplasmin and/or functional derivatives thereof to be used will vary according to factors such as the protein's biological activity, the type of condition being treated as well as the other ingredients in the composition. Typically, the amount of ceruloplasmin should vary from about 0.05 $\mu$M to about 20 $\mu$M. In a preferred embodiment, ceruloplasmin is present in the composition of the neuroprotective extracellular medium in an amount from about 0.05 $\mu$M to about 20 $\mu$M, preferably from about 0.1 $\mu$M to about 10 $\mu$M. In the most preferred embodiment, the neuroprotective composition comprises about 4 $\mu$M of highly active ceruloplasmin.

As stated out above, the neuroprotective composition of the invention comprises a therapeutically effective amount of ceruloplasmin or a functional derivative thereof, alone or in combination with an antioxidant. Preferably, the antioxidant has have a synergistic beneficial effect on neuronal cells when combined with ceruloplasmin, i.e. their combined effect is greater than the sum of their individual effects. More preferably, the antioxidant consist of catalase or of an amphiphilic antioxidative formulation comprising (a) pyruvate; (b) at least one antioxidant (such as vitamin E); and (c) at least one lipid (such as fatty acids).

The pyruvate in the present invention may be selected from the group consisting of pyruvic acid, pharmaceutically acceptable salts of pyruvic acid, prodrugs of pyruvic acid, and mixtures thereof. In general, the pharmaceutically acceptable salts of pyruvic acid may be alkali salts and alkaline earth salts. Preferably, the pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, $\alpha$-ketoglutaric acid, and mixtures thereof. More preferably, the pyruvate is selected from the group of salts consisting of sodium pyruvate, potassium pyruvate, magnesium pyruvate, calcium pyruvate, zinc pyruvate, manganese pyruvate, and the like, and mixtures thereof. Most preferably, the pyruvate is sodium pyruvate.

The amount of pyruvate present in the neuroprotective composition of the present invention is a therapeutically effective amount. A therapeutically effective amount of pyruvate is that amount of pyruvate necessary for the neuroprotective composition to prevent and/or reduce injury of a neuronal mammalian cell. The exact amount of pyruvate will vary according to factors such as the type of condition being treated as well as the other ingredients in the composition. Typically, the amount of pyruvate should vary from about 0.01 mM to about 100 mM. In a preferred embodiment, pyruvate is present in the composition of the neuroprotective extracellular medium in an amount from about 0.1 mM to about 30 mM, preferably from about 0.5 mM to about 10 mM. In the most preferred embodiment, the neuroprotective composition comprises about 10 mM of sodium pyruvate.

Antioxidants, including vitamin antioxidants, are substances which inhibit oxidation or suppress reactions promoted by ROS such as oxygen itself, oxygen free radicals, or peroxides. Antioxidants, especially lipid-soluble antioxidants, can be absorbed into the cell membrane to neutralize oxygen radicals and thereby protect the membrane. The antioxidants useful in the present invention may be selected from the group consisting of all forms of Vitamin A including retinal and 3,4-didehydroretinal, all forms of carotene such as alpha-carotene, $\beta$-carotene, gamma-carotene, delta-carotene, all forms of Vitamin C (D-ascorbic acid, L-ascorbic acid), all forms of tocopherol such as Vitamin E (alpha-tocopherol, 3,4-dihydro-2,5,7,8-tetramethyl-2-(4,8,12-trimethyltri-decyl)-2H-1-benzopyran-6-ol), $\beta$-tocopherol, gamma-tocopherol, delta-tocopherol, tocoquinone, tocotrienol, and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof. Preferably, the antioxidant is selected from the group of lipid-soluble antioxidants consisting of Vitamin A, $\beta$-carotene, Vitamin E, Vitamin E acetate, and mixtures thereof. More preferably, the antioxidant is Vitamin E or Vitamin E acetate. Most preferably, the antioxidant is Vitamin E acetate. Analogues of Vitamin E such as Trolox®, a compound which is more hydrosoluble than natural forms of Vitamin E and which could reach intracellular sites more rapidly, could also be used according to the present invention.

The amount of antioxidant present in the neuroprotective composition of the present invention is a therapeutically effective amount. A therapeutically effective amount of antioxidant is that amount of antioxidant necessary for the neuroprotective composition to prevent and/or reduce injury of a neuronal mammalian cell. The exact amount of antioxidant will vary according to factors such as the type of condition being treated as well as the other ingredients in the composition. Typically, the amount of antioxidant should vary from about 0.01 unit/ml to about 10 unit/ml. In a preferred embodiment, vitamin E antioxidant is present in the composition of the neuroprotective extracellular medium in an amount from about 0.01 unit/ml to about 10 unit/ml, preferably from about 0.05 to about 5 unit/ml. In the most preferred embodiment, the neuroprotective composition comprises about 1 unit of antioxidant (α-tocopherol type VI in oil) per ml of neuroprotective composition.

As it is well known, lipids are esters or carboxylic acid compounds found in animal and vegetable fats and oils. The composition may comprises a single type of lipid or various types of different lipids. Preferably lipids are in the form of a mixture of saturated and unsaturated fatty acids. However, other types of lipids could be used such as glycolipids and phospholipids (e.g. lecithin). Lipid(s) or mixture thereof are selected among those lipids required for the stabilization and/or repair of the membrane of neuronal mammalian cells. These lipids may be derived from animal or vegetables. In a preferred embodiment, selected lipids are in the form of mono-, di-, or triglycerides, or free fatty acids, or mixtures thereof, which are readily available for the stabilization or repair of the membrane of neuronal mammalian cells. Artificial lipids which are soluble in organic solvents and are of a structural type which includes fatty acids and their esters, cholesterols, cholesteryls esters could also be used according to the present invention.

In a more preferred embodiment, the saturated and unsaturated fatty acids are those deriving from egg yolk. According to the use of the neuroprotective compositions of the invention, replacing egg yolk as a source of fatty acids by chemical preparations of unsaturated, polyunsaturated and/or saturated fatty acids compatible with, and in proportions similar to those found in cell membranes may be advantageous or reveal necessary to insure a controllable quality of preparations.

The amount of lipid(s) such as fatty acids present in the neuroprotective composition of the present invention is a therapeutically effective amount. A therapeutically effective amount of fatty acids for instance is that amount of fatty acids necessary for the neuroprotective composition to prevent and/or reduce injury of a neuronal mammalian cells. The exact amount of lipid(s) or fatty acids will vary according to factors such as the type of condition being treated as well as the other ingredients in the composition. Typically, the amount of lipid(s) or fatty acids should vary from about 0.001% v/v to about 1% v/v. In a preferred embodiment, fatty acids are present in the neuroprotective composition in an amount from about 0.001% v/v to about 0.3% v/v, preferably from about 0.005% v/v to about 0.1% v/v. In the most preferred embodiment, the neuroprotective composition comprises about 0.1% v/v of fresh egg yolk.

As the lipidic blood level of an individual is normally about 0.5–0.6% of the total serum volume, the lipidic portion could be omitted from the neuroprotective composition of the invention. It could be possible to provide into the blood circulation of this individual at least one lipid having a synergistic therapeutic effect on neuronal cells with the others component of the antioxidative neuroprotective composition of the invention. For instance, selected lipid(s) could be provided by increasing the lipidic blood level ratio of this individual through the diet. Lipids which could have a synergistic therapeutic effect without being harmful to a patient could be selected from the group consisting of phospholipids, glycolipids, fatty acids, and mixture thereof.

Further agents can be joint to the neuroprotective composition of the invention. For examples various antioxidants may complete the action of neuroprotective composition such as:

- metal chelators/scavengers (e.g. desferrioxamine [Desferal®], a small substance capable to scavenge $Fe^{3+}$ and other metal ions);
- proteins or their fragments that can bind metal ions such as ferritin or transferrin which both bind $Fe^{3+}$);
- small scavengers of $\bullet O_2^-$ (superoxide), $\bullet OH$ (hydroxyl) or NO (nitric oxide) radicals (e.g. acetyl salicylic acid, scavenger of $\bullet O_2^-$; mannitol or captopril, scavengers of $\bullet OH$) or molecules that inhibit the generation of these radicals (e.g. arginine derivatives, inhibitors of nitric oxide synthase which produce NO);
- proteins or their fragments that scavenge oxygen free radicals and can assist the protective action of ceruloplasmin (e.g. superoxide dismutase which dismutate $\bullet O_2^-$; hemoglobin which traps NO); and
- proteins or their fragments that can scavenge $H_2O_2$ (hydrogen peroxide) in cases where they may exert a more potent or durable protective action than pyruvate (e.g. catalase, glutathion peroxidase).

The compositions of the invention may also comprise modulators of brain functions such as neurotransmitters, neuropeptides, hormones, trophic factors, or analogs of these substances that act by binding to brain receptors (e.g. DOPA in Parkinson's disease).

Further to the therapeutic agents, the pharmaceutical compositions of the invention may also contain preserving agents, solubilizing agents, stabilizing agents, wetting agents, emulsifiers, sweeteners, colorants, odorants, salts, buffers, or coating agents. For preparing such pharmaceutical compositions, methods well known in the art may be used.

The method of preparation of the neuroprotective composition of the invention is very simple as it consists simply in the mixing of purified ceruloplasmin and others of component(s) if any in a buffered saline solution in order to get a homogenous physiological suspension. Suitable saline solution comprises sodium, potassium, magnesium and calcium ions at physiological concentrations, has an osmotic pressure varying from 280 to 340 mOsmol, and a pH varying from 7.0 to 7.4. Depending of the amount and of type of lipid(s) which is used, the saline may also comprises an emulsifier. Preferably, the buffered saline solution is selected from the group consisting of modified Krebs-Henseleit buffer (KH) and phosphate buffer saline (PBS), both at pH 7.4. The homogenous suspension obtained can further be centrifuged and/or filtered to reduce its viscosity and/or eliminated non-soluble particles.

Obviously, this simple method can be modified according to the uses and the components constituting the neuroprotective composition. However, it is important to note that modifications in the modality of preparation can influence the resulting effects of the neuroprotective composition. For example, varying the pH of the composition (or buffer) can slightly modify the ionization state of carboxylic functions of pyruvate (if any) and thus alter its solubility and/or reaction with $H_2O_2$, while the dialysis of the composition would reduce the amount of pyruvate in the final preparation, unless it is done before addition of pyruvate. A person skilled in the art will know how to adapt the preparation of the neuroprotective composition of the invention according to their desired use in specific conditions in order to obtain positive effects.

The neuroprotective compositions of the invention could be suitable to treat diseases and pathological conditions such as brain trauma and diseases which were shown to involve oxidative stress conditions such as amyotrophic lateral sclerosis and neurodegenerative Parkinson's, Alzheimer's and Huntington's diseases. These neuroprotective compositions could also be involved in the treatment of poisoning or diminution of side effects of drugs (such as chemotherapeutic and immunosuppressive drugs) to the brain and/or to neuronal cells. Indeed, deleterious action of various toxicants and drugs is exerted via production of ROS.

The neuroprotective compositions of the invention have potential applications in both fast and long term treatments. The amount to be administered is a therapeutically effective amount. A therapeutically effective amount of a neuroprotective composition is that amount necessary for protecting a neuronal cell from the loss of viability or function induced by a toxic substance, stabilizing the membrane of neuronal cells and/or helping in the normalization of neuronal cell functions. Suitable dosages will vary, depending upon factors such as the type and the amount of each of the component(s) in the composition, the desired effect (fast or long term), the disease or disorder to be treated, the route of administration and the age and weight of the individual to be treated.

Obviously, the neuroprotective composition of the invention may be administered alone or as part of a more complex pharmaceutical composition according the desired use and route of administration. Anyhow, for preparing such compositions, methods well known in the art may be used.

The neuroprotective composition of the invention and/or more complex pharmaceutical compositions comprising the same may be given via various route of administration. Ways that can be considered are rectal and vaginal capsules or nasally by means of a spray. They may also be formulated as creams or ointments for topical administration. They may also be given parenterally, for example intravenously, intramuscularly or sub-cutaneously by injection or by infusion. Intravenous administration can be a way for fast answer in various clinical conditions (e.g. brain trauma, brain and cerebrovascular ischemia, stroke and heart attacks, post-surgery treatments, etc). Obviously, the neuroprotective composition of the invention may be administered alone or as part of a more complex pharmaceutical composition according to the desired use and route of administration. Anyhow, for preparing such compositions, methods well known in the art may be used.

The neuroprotective composition could be administered per os (e.g. capsules) depending of its composition (i.e. to do so all composition's components must be absorbable by the gastrointestinal tract). For example, CP as such cannot be recommended for oral administration because, as a large molecule, it would not be intestinally absorbed. This may not however apply to smaller and/or functional derivatives of this protein provided their formulation in absorbable forms (e.g. liposomes). Intravenous injection/perfusion and nasal sprays are possible ways to administer the composition of the invention.

As it will now be demonstrated by way of an example hereinafter, the composition of the invention possess a strong neuroprotective activity i.e. the capacity to maintain the viability and functions of neurons at their normal level or to induce a fast recovery to the normal level, even in pathological or harmful conditions such as oxidative stress conditions. These conditions can occur at post-ischemia reperfusion of the brain associated with an attack to brain vasculature, cerebral trauma, heart stroke/attack, in various neurodegenerative diseases, in epilepsy, exposure to neurotoxicants, or as side-effects of drugs and inflammation. Although any method and material similar or equivalent to those described herein can be used in the practice or testing of the present invention, the preferred methods and materials are described.

EXAMPLE

Neuroprotective Actions of Ceruloplasmin Against Oxidative Stress and its Synergistic Actions Against Oxidative Stress When Used in Combination with TRIAD Abstract Oxidative stress, in particular that induced by ischemia and reperfusion, remains a major cause of acute brain injuries, leading to neurological dysfunctions. In addition, oxidative stress is also involved in the evolution of various neurodegenerative diseases. It has been shown previously that Ceruloplasmin (CP), a multifunctional blue-copper plasma protein which has important antioxidant and free oxygen radical scavenging properties as well as a ferroxidase I activity, protects ischemic isolated rat heart against fibrillations due to reperfusion. The Inventors have shown in another study that TRIAD, a combination of sodium pyruvate, vitamin E and fatty acids, protects cultured P19 neurons against death caused by exposure to various prooxidant systems, including the xanthine/xanthine oxidase (XA/XAO) system which produces $\bullet O_2^-$ superoxide radicals and $H_2O_2$, the $H_2O_2$ hydrogen peroxide system, and the $H_2O_2/Fe^{2+}$ system which forms $\bullet OH$ hydroxyl radicals. These systems generate major reactive oxygen species that naturally occur during ischemia-reperfusion events (such as those occurring in brain stroke or trauma, in heart stroke or attack, as exemple).

In the present study, the P19 neuron model was used to determine whether CP as by itself provides protection and whether CP in association with an antioxidant formulation such as TRIAD provides higher protection against oxidative stress damages than that observed for each agent alone. Neuronal protection was evaluated by measurement of cell viabilitiy after exposure to XA/XAO, $H_2O_2$ and $H_2O_2/Fe^{2+}$ systems. CP (4 $\mu$M) and TRIAD individually protected neurons against oxidative stress induced by XA/XAO. Surprisingly, the combination of both agents offered additive, and perhaps more than additive, protection when oxidative stress was more pronounced. Increased protection likely resulted from the complementary action of these agents since CP was shown to scavenge $\bullet O_2^-$ radicals in vitro while TRIAD contains pyruvate, a known scavenger of $H_2O_2$. In support of this, replacement of TRIAD by catalase, which inactivates $H_2O_2$, also yielded to higher neuroprotection than CP or catalase alone. In contrast to TRIAD, CP (4 $\mu$M) did not offer evident protection to neurons exposed to $H_2O_2$ and $H_2O_2/Fe^{2+}$ systems. In addition, CP did not either enhance the neuroprotective effect of TRIAD in those systems. When CP was incubated in the presence of $H_2O_2$ in vitro, it lost up to 70% of its ferroxidase activity, while the addition of pyruvate partly prevented CP inactivation. These results indicate that CP may be a target of the deleterious effect of $H_2O_2$ in vivo, and that scavengers of hydrogen peroxide can help to preserve CP function/integrity. The antioxidant capacity of CP and TRIAD in vitro was also analyzed by evaluating the extent to which they inhibit the oxidation of N,N-diethyl-p-phenylendiamine induced by $H_2O_2$ and $H_2O_2/Fe^{2+}$. In both systems, CP 4 $\mu$M did not exhibit evident antioxidant activity. In the $H_2O_2/Fe^{2+}$ system however, CP 13 $\mu$M showed antioxidant activity by itself and also increased the antioxidant action of TRIAD possibly, in part, via its ferroxidase activity.

Altogether, the results of this study indicate that CP offers a neuroprotective action and that combination of CP+TRIAD provides higher antioxidant capacity to than each agent alone. Therefore, this study demonstrates that enhanced neuroprotection can result from complementary spectrum of antioxidant properties and from mutual preservation of antioxidant activity/integrity.

1. Introduction 1.1 Ceruloplasmin—a multifunctional copper protein

Ceruloplasmin (CP) is an important plasma blue-copper protein ($\alpha_2$-globulin) with a multifunctional role (Gutteridge and Stocks, 1981). First of all, CP is the main copper carrier. As oxidase (EC 1.16.3.1), CP is involved in the regulation of the level of biogenic amines and phenols. Also known as Ferroxidase I, CP catalyses the $Fe^{2+} \rightarrow Fe^{3+}$ reaction (an important reaction considering that $Fe^{2+}$ catalyze the Fenton reaction which produces the highly toxic •OH radical from $H_2O_2$). Ceruloplasmin was also shown to be an important oxygen free radical (OFR) scavenger. Recently, CP was shown to be involved in angiogenesis, in relation with its function as copper carrier. In collaboration with the groups of Dr. Reginald Nadeau and Dr. Rui Wang (Univ. de Montréal), the Inventors have discovered several unexpected physiological functions of copper proteins. The studies on these new functions, as cardioprotective and antifibrillatory actions, as well as modulation of ionic channels in neurons (Wang et al., 1995), contributed to the knowledge on the CP biochemical and physiological roles, interesting for their possible therapeutic applications.

1.1.1 Ceruloplasmin and human pathology

Several diseases (Menkes, Wilson) are related to major alterations in the level of CP (DiDonato and Sarkar, 1997; Shas and Petrukhin, 1997). Evolution of these diseases appears related to the CP level, in particular with the holo-CP (CP completely loaded with copper), underlining the essential role of CP as copper carrier. On the other hand, there are more and more data suggesting that oxidative stress is an etiologic factor in Parkinson's, Alzheimer's and other neurodegenerative diseases, whose evolution could be influenced by level of iron in brain (Gitlin, 1998; Halliwell and Guttteridge, 1989). The possible involvement of this metal in neurodegenerative diseases, particularly in Parkinson's disease, and the recent association of systemic hemosiderosis (aceruloplasminmia) with a mutation in the human CP gene (Harris et al., 1995; Morita et al., 1995; Miyajima et al., 1998, Miyajima and Gitlin, 1996), supports the idea that the dominant role of this protein is that of a ferroxidase.

1.1.2 Ceruloplasmin biochemistry

The "blue copper" center of CP has a characteristic absorption band at 610 nm and a two-copper pair is diamagnetic detectable and another copper is EPR (electronic paramagnetic resonance) detectable. Ceruloplasmin contains six copper atoms per molecule. Three copper atoms are aggregated in a cluster which is the Blue-Copper center of CP. Two others form a diamagnetic pair. The last one is paramagnetic (EPR detectable).

An absorbency ratio $A_{610nm}/A_{280nm}=0.040$ was considered in the literature as characteristic of a homogeneous standard pure enzyme. It was reported for CP a high susceptibility at proteolysis, and physiological properties influenced by the molecular integrity. Despite intensive research in various laboratories, many aspects of CP are still unclear. The protein has been the object of many controversies (originated from its high susceptibility at proteolysis) concerning the molecular characteristics and the copper content. Also controversial was its complex physiological role as antioxidant/prooxidant (Gutteridge, 1994; Chahine et al., 1991; Fox et al., 1995). Within the last decade, a continuously growing interest concerns the molecular mechanisms of protection at cellular and tissular level, induced by CP.

It was recently shown that CP structure comprises six domains. Surprisingly, its configuration appears close to that of clotting Factor VIII. However, the enigma is not ended. The intriguing fact is that CP receptors were identified, localized in tissues strongly involved in oxidative processes (heart) or sensitive to oxidative stress (brain: known to be damaged by the oxidative stress, especially in aging). It is now established the presence of specific ceruloplasmin receptors, with specific localization in aorta and heart, in brain, on erythrocytes and recently reported, on placenta (Fisher and Goods, 1994; Barnes and Frieden, 1984; Orena et al., 1986, Stevens et al., 1984). Liver endothelium was shown to bind, transport and desialate CP, which is then recognized by galactosyl receptors of hepatocytes. Also it was shown the secretion of CP by lung, brain (astrocytes), etc. What is the real role of this noncirculant CP, is still to elucidate.

A questionable aspect is if CP (132 kDa) can be internalized as the whole molecule or as fragments. Chudej et al (1990) reported the transcytosis of exogeneous superoxide dismutase (SOD) and even of catalase (240 kDa) from coronary capillaries into dog myocytes. This is a particular case and a complete answer is not yet available for other cell or tissue types. In any case, an interaction of CP with cells was supposed.

1.2 ROS scavenging capacities of ceruloplasmin in vitro

It was found that CP has better antioxidant and cardioprotective capacities than SOD (Dumoulin et al., 1996). Furthermore, CP was compared, in terms of antioxidant potential in vitro, with other well established antioxidants, using β-phycocyanin as a fluorescent indicator protein (Atanasiu et al., 1998). It was found, again, that CP exhibits a better scavenging capacity than SOD and than deferoxamine (Desferal™, an antifibrillatory agent acting as an iron chelating agent). The concentrations of CP ensuring good antioxidative activity in vitro was for the range 2–15 $\mu M$ (Atanasiu et al., 1998), while albumin as control exhibited a similar antioxidative action at a concentration much higher (260 $\mu M$).

1.3 Cardioprotective and cardiomodulatory actions of ceruloplasmin

Some of the Inventors (in collaboration with Dr. R. Nadeau at the Research Center of the Sacré-Coeur Hospital and at Université de Montréal) were the first to show a cardioprotective effect of CP in conditions of oxidative stress (Chahine et al., 1991; Mateescu et al., 1995; Dumoulin et al., 1996). This was achieved using the model of isolated rat heart exposed to ROS that were generated by buffer electrolysis. Furthermore, CP was shown to exert an antifibrillatory effect at reperfusion of ischemic isolated hearts (Atanasiu et al., 1995). This aspect is important because the ischemia-reperfusion conditions that were used with rat hearts resemble those observed in human heart pathology. In part, the mechanism of cardioprotection can likely be explained by antioxidant properties of CP which can limit the damages done to the heart by the oxidative stress conditions that prevail at reperfusion. However, CP was also shown to behave as a Class III antiarrhythmic drug since it induced a prolongation of the effective refractory period (ERP) and of the action potential (AP) of rat hearts, in absence of oxidative stress (Atanasiu et al., 1996), indicating that some other properties of CP are involved in cardioprotection.

1.4 Action of ceruloplasmin on neuronal cells

Ceruloplasmin was recently shown to exert a neuromodulatory action on neuroblastoma cells (Wang et al., 1995). Indeed, the protein acts as a membrane depolarizing factor and as a inhibitor of $K^+$ channels in those cells (Wang et al., 1995). It is worth to mention that, in the model of isolated hearts, CP causes a prolongation of the effective refractory period (ERP) and behaves as a class III antifibrillatory drug (Atanasiu et al., 1996). These effects occur in conditions without oxidative stress and may involve the action of CP on heart receptors and/or $K^+$ channels.

Ceruloplasmin may also exert a protective effect on sympathetic nervous endings in isolated heart since it was shown to decrease catecholamine release induced by oxidative stress conditions applied to this organ (Chahine et al., 1991). The potential of CP to offer antioxidant protection to neurons of central nervous system (CNS) has never been determined, maybe for a reason among others, that it was judged physiologically irrelevant. Indeed CP, a circulating protein which likely cannot pass the blood-brain barrier, was not viewed as a natural resident of the brain. This aspect of CP function is now gaining importance due to the recent discovery of the synthesis of this protein in this organ (Klomp et al., 1996a, 1996b). Indeed a rare genetic disease associated with expression of a truncated, non functional form of the protein causes diabetes, important accumulation of iron in brain and liver, as well as neurological anomalies and degenerescences (Harris et al., 1995). These defects led to the proposal that CP plays an essential role in iron metabolism (Harris et al., 1995).

Concentration of CP in brain is not known but can conceivably attain values that are not negligible in the neighborhood of neurons since the protein is linked to the surface of astrocytes by a glycophospholipid anchor (Patel and David, 1997). Having ROS scavenging capacities as well as ferroxidase activity, CP could likely exert neuroprotective effects in oxidative stress conditions. This aspect is important and, at our knowledge, is for the first time approached in this study. In addition to its possible neuroprotective role, CP could also be a neuromodulatory factor of neurons of CNS. Little is known on relations that could exist between iron and copper metabolisms in mammals but in yeast, the iron transporter Fet 3 has ferroxidase activity and requires copper for its function (Mukhopadhyay et al., 1998). Iron and copper must be provided in sufficient amounts to mammalian brain because these metals are required by enzymatic systems responsible for neuron myelinisation and for synthesis of various neurotransmitters and neuropeptides. Before discovery of CP expression in brain, a depolarizing action of the protein on plasma membranes of neuroblastoma cells was demonstrated, suggesting a role for CP as a brain endogenous depolarizing factor (Wang et al., 1995).

1.5 A single-step chromatographic method for the fast purification of ceruloplasmin Recently, a novel single-step chromatographic method have been reported for the fast purification of ceruloplasmin, a method leading to a purified, electrophoretically homogeneous protein (Wang et al., 1994). Ceruloplasmin is susceptible to proteolytic denaturation and this fast method therefore protects CP against such denaturation by decreasing time of eventual contact with proteolytic enzymes found in plasma or blood. The purification procedure is based on the highly selective retention of CP on Amino-ethyl (AE)-agarose (see Mateescu et al 1999, for details concerning the CP purification schema). Using this procedure, it is possible to obtain CP preparations with ratio $A_{610}/A_{280}$=0.045–0.070 and a very high oxidasic activity. The purification method permits to minimize the risk of protein degradation (it is possible to obtain a substantially pure and non fragmented CP). In fact it is supposed that, following a reexamination of CP spectral properties (EPR [Calabrese et al., 1988]), that CP purified using this procedure is closer to its real native structure than commercial CP obtained by other methods. This method allows to realize an original CP immobilization. The conjugation of CP with biocompatible polymers is important because the immobilized enzyme conjugates show sought-for advantages such as higher stability, lower antigenicity and possibility to continuous use in various devices of potential interest for bioimplants or for organ preservation in view of transplantation.

1.6 Cardioprotective and neuroprotective actions of TRIAD

As stated herein before, TRIAD is a combination of pyruvate, antioxidant and fatty acids for which many uses have been patented. TRIAD comprises sodium pyruvate, vitamin E and egg yolk fatty acids. Although this combination is also known under the name of CRT (Cellular Resuscitation Therapy), the current denomination of TRIAD is use herein. The three components were shown to act synergistically to ameliorate wound healing (Martin, 1994, 1996; Sheridan et al., 1997) and to reduce oxidative damage to keratinocytes and monocytes exposed to ultraviolet light (Martin, 1996) or to hepatocytes treated with doxorubicin (Gokhale et al., 1997). In another study the Inventors have shown that TRIAD offers antioxidant protection to cultured P19 neurons exposed to prooxidant systems that generate major ROS produced by ischemia-reperfusion conditions in vivo. In addition, the Inventors also reported that TRIAD protects isolated rat hearts perfused with electrolyzed buffer or subjected to partial ischemia and reperfusion.

1.7 Presentation of the study

The objective of this study was first to determine if CP has an antioxidant protective action on cultured P19 neurons exposed to oxidative stress, as it was already shown for the isolated rat heart model. P19 neurons are an established model of neurons of the central nervous system. In addition, the neuroprotective action of CP in combination with other antioxidants such as TRIAD was also evaluated in order to determine if superior protection can be obtained by using antioxidants that could exert complementary actions. In this study, resistance of neurons to injury induced by oxidative stress was assessed by measurement of cell viability. When applicable, the antioxidant properties of CP and CP+TRIAD in vitro was also measured in order to understand some aspects of the protection they afforded to cells.

2. Materials and Methods

Materials

Vitamin E (α-tocopherol type VI in oil), sodium pyruvate, ethylenediamine tetraacetic acid (EDTA), N,N-diethyl-p-phenylenediamine (DPD), and xanthine (XA) were purchased from Sigma Chem. Co. Xanthine oxidase (XAO) was from Boëhringer Mannheim. Neurobasal®, L-glutamine and B27 supplement were from Gibco-BRL. Alamar Blue was purchased from Medicorp (Montréal, Québec). Fresh egg yolk was the source of fatty acids. The other current chemicals were reagent grade (from Sigma Chem. Co., St-Louis) and were used without further purification.

Methods 2.1 Preparation of ceruloplasmin

Ceruloplasmin was purified from bovine serum as already described (Wang et al., 1994; Mateescu et al., 1999), using an one-step affinity chromatography on aminoethyl-agarose. The value of $A_{610\ nm}/A_{280\ nm}$ was approximately 0.045 for all preparations used in this study. CP was stored at $-20°$ C. in 0.1M potassium phosphate buffer, pH 7.4. It was added as a solution in its storage buffer to culture medium of P19 neurons. In control studies, it was extensively dialyzed against phosphate buffer saline (PBS; 136 mM NaCl, 2.7 mM KCl, 1.5 mM KH$_2$PO$_4$ and 8 mM Na$_2$HPO$_4$, pH 7.4) before addition to cell culture medium in order to decrease the concentration of potassium ions present in storage buffer. Cellular responses to non-dialyzed and dialyzed CP were similar.

2.2 Preparation of TRIAD

The 1× TRIAD concentration was prepared as per Gokhale et al. (1997) and contained 0.1% v/v fresh egg yolk as the source of fatty acids, 1 unit/ml vitamin E (α-tocopherol type VI in oil) and 10 mM sodium pyruvate. Stock 5× (5 fold) or 10× (10 fold) concentration of TRIAD was freshly prepared before each experiment by carefully mixing the three agents to get a homogenous suspension. TRIAD mixtures were made in phosphate buffer saline (PBS; 136 mM NaCl, 2.7 mM KCl, 1.5 mM KH$_2$PO$_4$ and 8 mM Na$_2$HPO$_4$, pH 7.4). Pyruvate was soluble in and egg yolk miscible with this saline physiological buffer. Aseptically drawn egg yolk and vitamin E suspension (vitamin E in oil combined to 70% ethanol in a 2.5:1 ratio) were added at the desired final concentrations to a 100 mM stock pyruvate solution prepared in PBS and filter-sterilized on 0.22 μm.

Although not tested in this study, a modified preparation of TRIAD was shown to be effective to protect isolated hearts. Modifications of TRIAD preparation was modified as follows: 5× or 10× genuine preparations were centrifuged at 15000×g for 20 min, at 4° C., and the resulting supernatants (S1) filtered on Whatman paper filter #54. The final filtered supernatant was named TRIAD (S2) and used to perfuse hearts. The different concentrations of TRIAD (S2) preparation were obtained by subsequent dilution with Krebs-Hesseleit physiological saline buffer (i.e. TRIAD (S2) 1× was obtained by 10 fold dilution of stock TRIAD (S2) 10× preparation).

2.3 Culture and neuronal differentiation of P19 cells

Culture and neuronal differentiation of P19 embryonal carcinoma cells were done according to the procedures of Jeannotte et al. (1997) with the following modifications for microscale adaptation of cultures to 96-well plates: cell aggregates obtained at day 4 of the treatment of P19 cells with retinoic acid were trypsinized with 0.025% trypsin-1 mM EDTA in PBS and subjected to mechanical passages to obtain individual cells which were seeded in gelatin-precoated microwells at a density of 0.7–1×10$^5$ cells per well. The newly seeded cells (neurons) were cultured in supplemented Neurobasal medium (Neurobasal® containing 0.5 mM L-glutamine and 0.5% B27 supplement) until exposure to oxidative conditions at day 7. Because this defined serum-free medium sustains growth of P19 neurons (Yao et al., 1995) but discourages the proliferation of fibroblasts, another cell derivative of the differentiation of P19 cells with retinoic acid (McBurney, 1993; Jeannotte et al., 1997), the cell populations in microwells were composed mostly of neurons ($\geq$95%).

2.4 Studies on P19 neurons exposed to ROS naturally produced in ischemia-reperfusion P19 neurons were exposed to the following prooxidant systems: i) XA/XAO system (which produces •O$_2^-$ superoxide radicals and hydrogen peroxide H$_2$O$_2$, according to equation 1, shown below); ii) hydrogen peroxide H$_2$O$_2$; and iii) H$_2$O$_2$/Fe$^{+2}$ system (which generates •OH [hydroxyl radicals] via the Fenton reaction, equation 2). When CP and CP+TRIAD were tested for their antioxidant action, they were administered to cells just prior the addition of XAO or H$_2$O$_2$. The order of addition was therefore as follows: i) PBS, TRIAD, CP, XA, and finally XAO for the XA/XAO system, ii) PBS, TRIAD, CP, and then H$_2$O$_2$ for the H$_2$O$_2$ system, and iii) PBS already containing Fe$^{+2}$, TRIAD, CP, and finally H$_2$O$_2$ for the H$_2$O$_2$/Fe$^{+2}$ system. After they were incubated under oxidative conditions, neurons were analyzed for their residual viability by a fluorimetric assay using the Alamar Blue probe (see section 2.5).

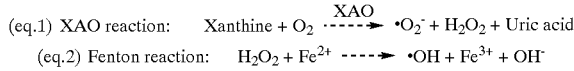

(eq.1) XAO reaction: Xanthine + O$_2$ $\xrightarrow{\text{XAO}}$ •O$_2^-$ + H$_2$O$_2$ + Uric acid (eq.2) Fenton reaction: H$_2$O$_2$ + Fe$^{2+}$ $\dashrightarrow$ •OH + Fe$^{3+}$ + OH$^-$ Before neurons were exposed to either one of these systems, they were carefully washed with PBS and then incubated at 37° C., in an atmosphere of 95% ambient air and 5% CO$_2$, and in the specific conditions of each system. Conditions were adapted from Cini et al. (1994) for XA/XAO, from Desagher et al. (1996) for H$_2$O$_2$, and from Takemura et al. (1994) for the H$_2$O$_2$ and H$_2$O$_2$/Fe$^{+2}$ systems respectively.

There were two sets of conditions for the XA/XAO system. To achieve pronounced oxidative stress conditions with this system, cells were incubated for 40 min in PBS containing 250 μM XA and concentrations of XAO varying from 0 to 12.5 mU/mL (with the enzyme added last to start the reaction), then for 16 h in a fresh provision of supplemented Neurobasal-minus AO medium (i.e. Neurobasal medium containing the B27 supplement from which all antioxidants were removed, Gibco-BRL) and, finally, for a last 7 h period in the same Neurobasal medium but containig Alamar Blue for the determination of viability. Milder oxidative stress conditions were achieved by omitting the 16 h incubation period. For H$_2$O$_2$ and H$_2$O$_2$/Fe$^{2+}$ systems, cells were incubated during 30 min in PBS containing 0 to 9 mM H$_2$O$_2$, respectively without or with 50 μM FeCl$_2$ (peroxide was always added last). Afterwards, cells were incubated for 7 h in a fresh provision of supplemented Neurobasal-minus AO medium containing Alamar Blue. In all cases, TRIAD and/or CP were present in the incubation medium during the stress period only.

The protective effect of catalase (84 U) was also tested in the place of TRIAD. Catalase enzyme converts hydrogen peroxide into water, and the amount used was more than sufficient to afford 100% protection to neurons exposed to 5 mM hydrogen peroxide during 30 min.

2.5 Cell viability assay

After they were incubated under oxidative conditions, neurons were analyzed for their residual viability by a fluorimetric assay using the Alamar Blue probe. Briefly, fifteen (15) μl Alamar Blue was added to the culture medium of each well (200 μl) and incubation resumed for 7 h at 37° C., 5% CO$_2$. A 180-μl aliquot of each culture medium was read by fluorescence using a wavelength of 544 nm for excitation and of 590 nm for emission; fluorescence increases upon reduction of the dye by metabolic activity of viable cells. Fluorescence determinations were done with a fluorimeter adapted to read microplates. Viability is reported as %, comparing the fluorescence units obtained for cells exposed to oxidative conditions to those of control (non-exposed) cells.

2.6 In vitro antioxidant capacity

Oxidation of N,N-diethyl-p-phenylenediamine (DPD) by a prooxidant system was used as a general reporter of the amount of ROS generated by that system (Anonymous, 1985; Chahine et al., 1991). Antioxidant capacity of preparations of TRIAD (or of its components) was defined as the ability to inhibit the oxidation of DPD by prooxidants.

To estimate the antioxidant capacity of TRIAD preparations in the prooxidant conditions used with P19 neurons, DPD was added to a final concentration of 32 mM to 200 μl of each prooxidant system described above (see section 2.4) and incubated for the times tested with the cells. At the end of incubation, the amount of oxidized DPD was determined at 560 nm using a spectrophotometer adapted to microscale measurement.

2.7 Protective effect of pyruvate on ferroxidase activity of CP in vitro

CP (4 μM) was incubated for different times (ranging from 0 to 12 h) in the presence of 5 mM $H_2O_2$, at 37° C., in PBS, without or with the addition of pyruvate (5 mM) as a protecting agent. At the end of incubation, catalase was added at a concentration of 0.1 mg/ml (84 U/ml) and incubation resumed at room temperature for 15 min in order to inactivate $H_2O_2$. Ferroxidase activity of CP was then measured by absorbence using a modified version of the method of Erel (1998). This method uses a chromogen to complex $Fe^{2+}$ ions that were not transformed to $Fe^{3+}$ ions in the assay solution. The reaction mix contained 0.45M acetate buffer, pH 5.8, 60 μM $Fe(NH_4)_2(SO_4).6H_2O$, and either CP (sample), 25 mM EDTA (control corresponding to 100% iron oxidation) or PBS (control corresponding to 0% iron oxidation). Reaction was carried out during 30 min in wells of 96-well plates, and stopped by adding the chromogen (3-(2-pyridyl)-5,6-bis(2-[5-furylsulfonic acid]) which yields a complex with $Fe^{2+}$ that absorbs at 595 nm. Control studies in absence of CP indicated that there was no spontaneous oxidation of $Fe^{2+}$ by $H_2O_2$ following the addition of catalase 3. Results To determine if CP can protect P19 neurons against death caused by oxidative stress, a CP concentration of 0.5 mg/ml was used, a concentration that can be physiologically encountered in vivo. Indeed CP concentration in serum varies up to 300 μg/ml (2.4 μM) in normal conditions and can reach 700 μg/ml (5.3 μM) in acute inflammatory phases (Fox et al., 1995). The concentration of 500 μg/ml (4 μM) was found to be not toxic to P19 neurons; toxicity of higher concentrations was not tested.

Legends to the Figures

FIG. 1. Protection provided by CP and TRIAD to P19 neurons exposed to mild oxidative stress conditions mediated by XA/XAO. P19 neurons were exposed for 40 min to 250 μM XA and different concentrations of XAO in the absence (No protection) or presence of 4 μM (0.5 mg/mL) CP and/or 1× TRIAD. At end of stress, cells were incubated for 7 h in a fresh provision of culture medium lacking XA, XAO, CP and TRIAD, but containing Alamar Blue for viability determination. Viability values are reported as percentages, with 100% corresponding to the response of P19 neurons not exposed to XA/XAO. The experiment was done twice, in triplicate determinations, and results are expressed as means±errors to the means.

Figure 2:
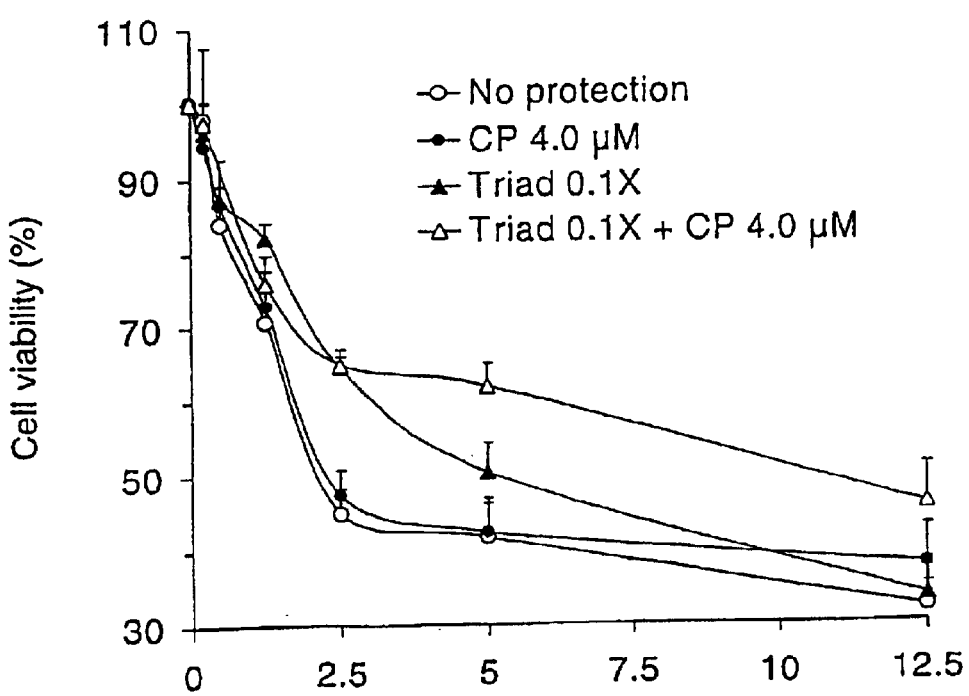
FIG. 2 is a graph showing the protection provided by CP and TRIAD to P19 neurons exposed to pronounced oxidative stress conditions mediated by XA/XAO.

FIG. 2. Protection provided by CP and TRIAD to P19 neurons exposed to pronounced oxidative stress conditions mediated by XA/XAO. P19 neurons were exposed for 40 min to 250 μM XA and different concentrations of XAO in the absence (No protection) or presence of 4 μM (0.5 mg/mL) CP and/or 0.1× TRIAD. At end of stress, cells were incubated for 16 h in a fresh provision of culture medium lacking XA, XAO, CP and TRIAD. Afterward, Alamar Blue was added and cells were further incubated for 7 h for viability determination. Viability values are reported as percentages, with 100% corresponding to the response of P19 neurons not exposed to XA/XAO. The experiment was done three times, in triplicate determinations, and results are expressed as means ±S.D.

Figure 3:
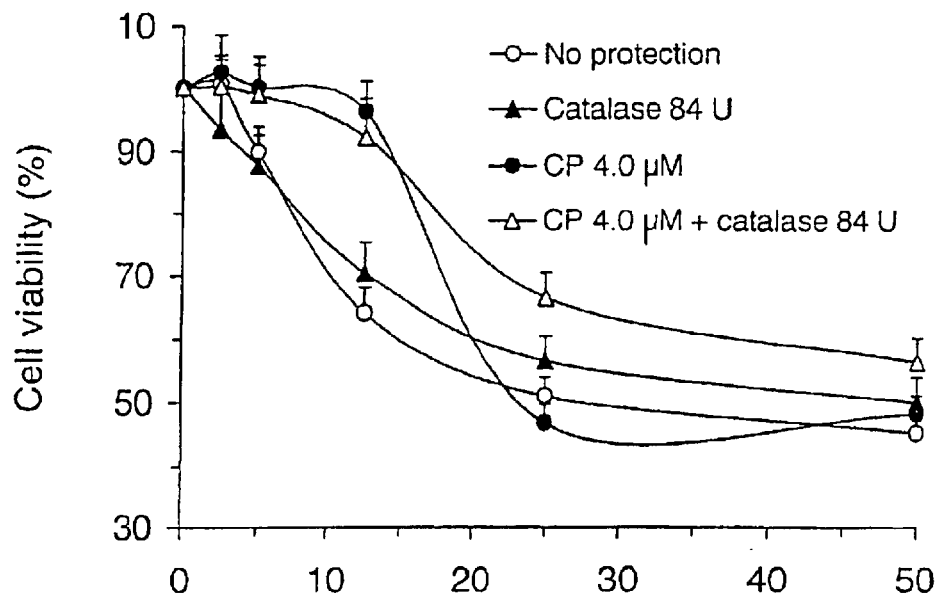
FIG. 3 is a graph showing the protection provided by CP and catalase to P19 neurons exposed to oxidative stress conditions mediated by XA/XAO.

FIG. 3. Protection provided by CP and catalase to P19 neurons exposed to oxidative stress conditions mediated by XA/XAO. P19 neurons were exposed for 30 min to 250 μM XA and different concentrations of XAO in the absence (No protection) or presence of 4 μM (0.5 mg/mL) CP and/or 84 U catalase. At end of stress, cells were incubated for 7 h in a fresh provision of culture medium lacking XA, XAO, CP and catalase, but containing Alamar Blue for viability determination. Viability values are reported as percentages, with 100% corresponding to the response of P19 neurons not exposed to XA/XAO. The experiment was done three times, in triplicate determinations, and results are expressed as means±S.D.

Figure 4:
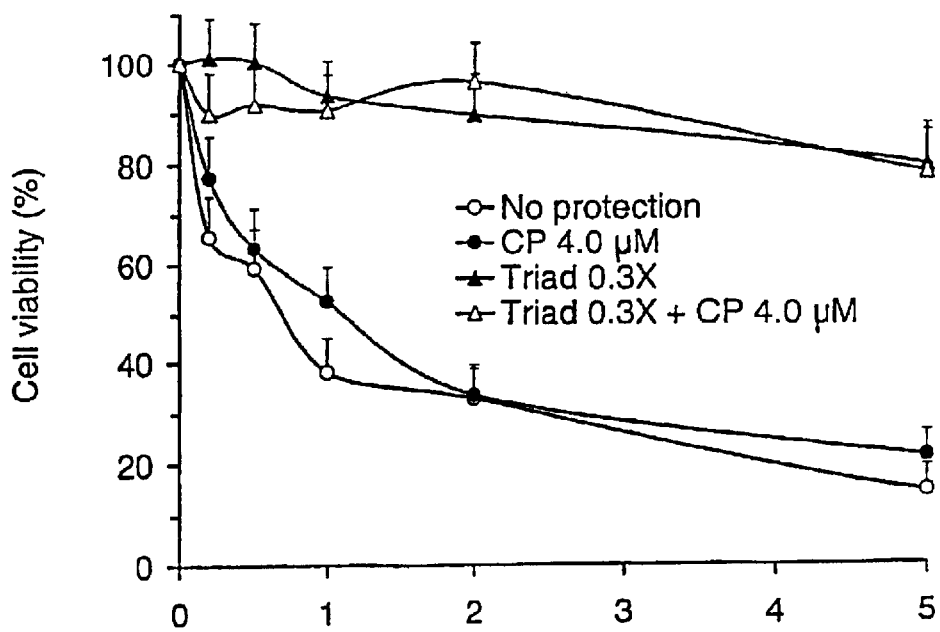
FIG. 4 is a graph showing the protection provided by CP and TRIAD to P19 neurons exposed to hydrogen peroxide mediated oxidative stress.

FIG. 4. Protection provided by CP and TRIAD to P19 neurons exposed to hydrogen peroxide mediated oxidative stress. Cells were exposed during 30 min to different concentrations of $H_2O_2$ in the absence (No protection) or presence of 4 μM (0.5 mg/mL) CP and/or 0.3× TRIAD. At end of stress, cells were incubated for 7 h in a fresh provision of culture medium lacking $H_2O_2$, CP and TRIAD, but containing Alamar Blue for viability determination. Viability values are reported as percentages, with 100% corresponding to the response of P19 neurons not exposed to $H_2O_2$. The experiment was done twice, in duplicate determinations, and results are expressed as means±errors to the means.

FIG. 5. In vitro antioxidant capacity of CP and TRIAD, in the conditions of $H_2O_2$ prooxidant system used with P19 neurons. In this assay, conditions of incubation were as described in the legend to FIG. 4 except that P19 neurons were replaced by N,N-diethyl-p-phenylenediamine (DPD) which absorbs at 560 nm upon oxidation. The experiment was done four times, in triplicate determinations, and results are expressed as means±S.D.

FIG. 6. In vitro antioxidant capacity of CP 4 μM and TRIAD in the conditions of $H_2O_2/Fe^{2+}$ prooxidant system. The oxidation of DPD was induced by incubation with different concentrations of $H_2O_2$ and 50 μM $FeCl_2$, during 30 min, at 37° C. The experiment was carried out in the absence (No protection) or presence of CP and/or TRIAD. Oxidized DPD was measured at 560 nm, at end of incubation. The experiment was done three times, in duplicate determinations, and results are expressed as means±S.D.

FIG. 7. In vitro antioxidant capacity of CP 13 μM and TRIAD in the conditions of $H_2O_2/Fe^{2+}$ prooxidant system. The study was identical to that described in FIG. 6, except that CP was used at 13 μM. The experiment was done three times, in duplicate determinations, and results are expressed as means±S.D.

FIG. 8. Protection of CP ferroxidase activity by pyruvate in vitro. CP was incubated for various times, at 37° C., in the presence of 5 mM $H_2O_2$, without (No protection) or with 5 mM sodium pyruvate. The reaction was stopped by a 5 min incubation with an excess of catalase. Ferroxidase activity was then measured and expressed relatively (%) to that of a control CP sample not exposed to $H_2O_2$. The experiment was done three times, in duplicate determinations, and results are expressed as means±S.D.

3.1 Neuroprotection afforded by CP and CP+TRIAD against oxidative stress induced by XA-XAO The XA/XAO system is known to generate superoxide radicals ($•O_2^-$) and $H_2O_2$. FIG. 1 shows that exposure of P19 neurons to increasing concentrations of XAO under mild oxidative stress conditions caused a gradual loss of viability (see the curve No protection). When CP was added at 0.5 mg/mL in the stress medium, it diminished cell mortality (FIG. 1). TRIAD 1× also offered neuroprotection, and protection was not further increased by adding CP to TRIAD (FIG. 1). Cell mortality was greater when we exposed neurons to harsher oxidative stress conditions with the same prooxidant system (compare the No protection curves of FIGS. 1 and 2). In the latter conditions, CP 0.5 mg/mL did not offer great protection while TRIAD still diminished cell mortality (FIG. 2). However, in contrast to the results obtained under mild conditions, the combination of CP and TRIAD now provided higher protection than that seen with each agent alone (FIG. 2). In fact, although the CP+TRIAD combination was as effective as TRIAD itself up to 2.5 mU/mL XAO, it then became more protective at higher concentrations of the enzyme. Moreover, the protection was apparently synergistically increased since it was superior than the strict summation of individual effects (FIG. 2).

One possible explanation to the increased neuroprotection achieved by combining CP and TRIAD is the complementary antioxidant properties of each agent. This explanation is well supported by the known capacity of CP to scavenge $\bullet O_2^-$ radicals in vitro (Atanasiu et al., 1998) and that of TRIAD (via pyruvate) to scavenge $H_2O_2$ (Martin, 1996; Gokhale et al., 1997). To add more support to this explanation, we replaced TRIAD by catalase, an enzyme which deactivates $H_2O_2$. Although the protocol was slightly different with catalase (FIG. 3) than with TRIAD (FIGS. 1 and 2), we still observed a cell mortality that increased at higher concentrations of XAO. Ceruloplasmin offered a protection that dropped abruptly at concentrations of XAO above 12.5 mU/mL, while catalase was protective up to 50 mU/mL of the oxidase (FIG. 3). Similar to TRIAD+CP, catalase+CP also provided higher neuroprotection than each agent alone at high concentrations of XAO (FIG. 3). This finding supports the hypothesis that more protection can result from the combination of complementary antioxidant properties. We could thus propose that a gain of protection can be achievable if CP is associated with a scavenger of $H_2O_2$.

As said in the above paragraph, increased neuroprotection was achieved by combining CP and TRIAD likely because these agents have complementary antioxidant properties, with CP scavenging $\bullet O_2^-$ and TRIAD (via pyruvate) scavenging $H_2O_2$ (Martin, 1996; Gokhale et al., 1997). The possible synergistic increase of neuroprotection by CP+TRIAD association, could also be due to protection provided to CP itself by TRIAD, against degradation mediated by $H_2O_2$. Islam et al. (1995) have shown that incubation of CP in the presence of 5 mM $H_2O_2$ can cause fragmentation of the protein. However, even if fragmentation occurred, it could have not affected the scavenging properties of CP versus $H_2O_2$. This reasoning is supported by studies done in vitro on the scavenging properties of native and denatured CP (Atanasiu et al., 1998). It was found that 12 $\mu$M CP was necessary to inhibit by 50% modification of $\beta$-phycocyanin by superoxide radicals while as low as 2 $\mu$M was necessary to produce the same effect with heat denatured protein (Atanasiu et al., 1998). In XA-XAO system, where hydrogen peroxide is released together with superoxide, it is possible that released peroxide inhibits native CP ability to scavenge superoxide. The situation is different for heat denatured CP, which was shown to expose more —SH groups (Atanasiu et al., 1998), potentially able to scavenge $H_2O_2$. These data, clearly demonstrated the ability of native CP to scavenge $\bullet O_2^-$ (superoxide), but did not give information on an eventual nonspecific hydrogen peroxide scavenging capacity. This is why we have chosen to investigate $H_2O_2$ scavenging capacity of native CP directly on neurons (see section 3.2). The effect of $H_2O_2$ on CP ferroxidase activity was also tested (see section 3.4).

3.2 Protection afforded by CP and CP+TRIAD against oxidative stress induced by $H_2O_2$ FIG. 4 shows that CP, at a concentration of 4.0 $\mu$M, protected P19 neurons only marginally against death caused by incubation in the presence of hydrogen peroxide, while TRIAD 0.3× afforded protection. In contrast to what observed in the XA/XAO system, the association of CP with TRIAD in the $H_2O_2$ system, did not enhance the protection exhibited by TRIAD alone (FIG. 4). This result indicates that CP, at the tested concentration, is not a good scavenger of hydrogen peroxide. This is also supported by in vitro analysis. In fact, 4.0 $\mu$M CP alone did not inhibit oxidation of DPD probe by $H_2O_2$, nor did it add to inhibition achieved by TRIAD (FIG. 5). These results are therefore consistent with CP intervening as a superoxide radical scavenger in XA/XAO system (section 3.1) and not as a hydrogen peroxide scavenger.

3.3 Protection afforded by CP and CP+TRIAD against oxidative stress induced by $H_2O_2/Fe^{2+}$ The $H_2O_2/Fe^{+2}$ was used system in order to reveal a possible participation of CP in neuroprotection against damages induced by hydroxyl radicals. These radicals can be formed from $H_2O_2$ in the presence of trace amounts of $Fe^{+2}$, according to the Fenton reaction (eq. 2, section 2.4). CP at 4.0 $\mu$M did not protect P19 neurons exposed to this prooxidant system and it did not either add to the protection provided by TRIAD (not shown).

The antioxidant in vitro capacity of CP in the $H_2O_2/Fe^{+2}$ system was also investigated. Addition of $Fe^{+2}$ increased the oxidant power of $H_2O_2$ as expected. Indeed, the absorbency at 560 nm caused by oxidation of the DPD probe plateaued at near 0.6 in the $H_2O_2$ system (FIG. 5, No protection) while it reached a value of 1.5 when $FeCl_2$ was added (FIG. 6, No protection). TRIAD but not CP 4 $\mu$M inhibited DPD oxidation induced by $H_2O_2/Fe^{2+}$ (FIG. 6). A similar inhibition to that of TRIAD was seen for the association of CP 4.0 $\mu$M and TRIAD (FIG. 6). However, an inhibition of DPD oxidation in this system was observed by using a higher concentration (13 $\mu$M) of CP (FIG. 7). The combination TRIAD+CP provided a higher inhibition of oxidation. The resulting effect was less than additive (FIG. 7). It is possible that CP ferroxidase activity was involved in the antioxidant capacity of the protein in the $H_2O_2/Fe^{2+}$ system. The fact that pyruvate added to this capacity would imply that CP can be a target of $H_2O_2$ deleterious action. This is supported by the study of Islam et al. (1995) who showed that exposure of CP to $H_2O_2$ in vitro caused the disappearance of the CP bands by electrophoresis, perhaps due to fragmentation of the protein by $\bullet OH$ radicals as suggested by the authors. However, $H_2O_2$ could also be detrimental to the ferroxidase activity at the first place.

3.4 Protective effect of pyruvate on CP ferroxidase activity in vitro

To begin to understand the potentially synergistic character of the neuroprotection afforded by CP and by TRIAD in XA/XAO system (section 3.1), the effect of $H_2O_2$ on CP ferroxidase activity in vitro was studied. FIG. 8 shows that CP can loss this activity when incubated with $H_2O_2$, and this loss increased with time of exposure. Interestingly, pyruvate, a scavenger of $H_2O_2$ present in TRIAD, inhibited the loss of ferroxidase activity induced by $H_2O_2$ (FIG. 8).

4. Discussion

This study is the first to report a neuroprotective action of CP. This study shows that CP alone increased survival of cultured P19 neurons when they were exposed to oxidative stress involving superoxide radicals (FIG. 1). In addition, as summarized in Table I below, association of CP and TRIAD provided synergistic protection to cultured neurons exposed to XA/XAO system (see also FIG. 2).

nonspecific interaction with hydrogen peroxide could be expected (i.e. —SH groups), a possible explanation of ferroxidase inactivation described above. On the other hand, Islam et al. (1995) have shown that $H_2O_2$ can also cause CP

TABLE I

Antioxidant protection afforded by the combination of Ceruloplasmin and TRIAD.

| | | Prooxidant system | |
|---|---|---|---|
| Model | XA/XAO | $H_2O_2$ | $H_2O_2/Fe^{2+}$ |
| Neurons | TRIAD, + | TRIAD, + | TRIAD, + |
| | CP (4 μM), + | CP (4 μM), − | CP (4 μM), − |
| | Combination, ↑↑ or ↑↑↑ | Combination, ≅ TRIAD | Combination, ≅ TRIAD |
| In vitro | Not determined* | TRIAD, + | TRIAD, + |
| | | CP (4 μM), − | CP (4 μM), − |
| | | Combination, ≅ TRIAD | Combination, ≅ TRIAD |
| | | | TRIAD, + |
| | | | CP (13 μM), + |
| | | | Combination, ↑ |

The results are presented for cultured P19 neurons and their in vitro counterpart (i.e. prooxidant conditions tested on DPD, in absence of cells). The symbols + and − respectively indicate that protection was observed or not. Combination of CP and TRIAD afforded protection that was either equivalent (≅) to that of TRIAD, or greater (↑, ↑↑, ↑↑↑) than that of each agent alone. The greater protection was apparently less than additive (↑), additive (↑↑) or synergistic (↑↑↑).
*not determined because the prooxidant system cannot directly oxidize DPD.

Since the XA/XAO system generates superoxide radicals and hydrogen peroxide, and since CP has recognized superoxide radical scavenging properties in vitro (Anastasiu et al., 1998) while TRIAD contains a scavenger (pyruvate) of hydrogen peroxide (Martin, 1996), it is concluded that higher protection was achieved with CP and TRIAD association due to their complementary antioxidant action. Interestingly, the study of Anastasiu et al. (1998) showed that as high as 12 μM CP was necessary to exhibit 50% antioxidant activity in XA/XAO system in vitro. This concentration was not tried with neurons because it appears unphysiological. However, FIGS. 1–3 suggest that physiologically relevant concentrations of CP and low concentrations of TRIAD can assist neurons in their efforts to assure their own protection, leading to the conclusion that higher efficiencies of protection would better be achieved with small concentrations of different antioxidants in association, than with saturating concentrations of a given one. It is possible that residual amounts of XA/XAO in the culture medium of P19 neurons actually lead to underestimate the neuroprotective action of CP, TRIAD, or their combinations. As was the case for CP and TRIAD on neurons, this study also permits to demonstrate that CP and catalase can have complementary action, the former acting on •$O_2^-$ (among other potential effects), the latter, on $H_2O_2$ (FIG. 3).

The almost absence of CP protective effect under harsh stress conditions mediated by XA/XAO (FIG. 2) can be due to either one or both effects: i) insufficient amounts of CP versus amounts of •$O_2^-$ generated, ii) loss of CP integrity. However, CP was shown to be a target of $H_2O_2$ (it lost its ferroxidase activity during exposure to this ROS; FIG. 8) and pyruvate was shown to inhibit the detrimental effect of $H_2O_2$ on CP in vitro (FIG. 8). Therefore, a part of the synergistic neuroprotection observed for CP+catalase and CP+TRIAD combinations can be explained by the protection directly afforded to CP itself by scavengers of $H_2O_2$. Differently to catalase, an enzyme which catalyses $H_2O_2$ decomposition with a high turnover number, CP appears to be a poor scavenger of hydrogen peroxide, although a degradation and also fragmentation, which can be prevented by addition of catalase and EDTA (a chelator of iron ions).

FIG. 3 potentially suggests an interesting finding: superoxide radical could be more detrimental to cells than hydrogen peroxide. Indeed, whereas 84 U catalase was sufficient to completely inhibit DPD oxidation induced by a 30 min exposure to 5 mM $H_2O_2$ (not shown), it provided only partial (about 10%) protection to neurons incubated for 40 min with XAO in the presence of 250 μM XA (FIG. 3), a condition that would generate 250 μM $H_2O_2$.

Considering the ferroxidase activity of CP as well as its •$O_2^-$ scavenging properties, the overall antioxidant action of the protein in vivo has the potential to greatly inhibit the generation of very toxic •OH radicals. Indeed, CP can decrease the amount of $Fe^{2+}$ ions that are necessary to feed the Fenton reaction. In addition, it can trap •$O_2^-$ radicals which are no longer available to reduce back $Fe^{3+}$ to $Fe^{2+}$ via the Haber-Weiss reaction, or to combine with •NO radicals to form peroxynitrite anions, and then •OH (Peuchen et al., 1997). Presence of hydrogen peroxide scavengers in such a treatment scheme, would be beneficial to CP action because of their possible inhibition of peroxide-induced CP degradation. Another possible mechanism of CP neuroprotective action can involve its action on cellular metabolism since receptors for this protein have been detected in various cells or tissues, including heart, brain and erythrocytes (Frieden, 1986; Stevens et al., 1984; Orena et al., 1986; Fischer and Goode, 1994). Two sets of experimental evidences support this hypothesis. Indeed, CP can act on neuronal $K^+$ channels (Wang et al., 1995) and can influence heart cardiodynamics (Chahine et al., 1991) in absence of oxidative stress. The possibility that CP can intervene in cell metabolism would require further investigation. In the lights of present knowledge, CP would be the major extracellular antioxidant enzyme in brain and would thus protect neurons against damages caused by leakage of ROS from neighboring cells (including other neurons). Indeed hydrogen peroxide easily crosses membranes, and superoxide radicals can be distributed between intra- and extracellular spaces using anion channels. In addition, ascorbate which is massively released by astrocytes as an important antioxidant in brain, can display prooxidant action in the presence of high concentrations of oxygen or of trace amounts of iron (Peuchen et al., 1997; Halliwell and Gutteridge, 1989).

5. Conclusive remarks

This study shows that CP can provide antioxidant protection to neurons exposed to ROS naturally produced by ischemia-reperfusion conditions, especially towards $\bullet O_2^-$ and $\bullet OH$. In addition, CP+TRIAD reciprocally enhance both their neuroprotective actions, and comparison of their individual profile of action in cultured neurons suggests that this enhancement is likely due to their complementary antioxidant capacities. Enhanced protection can have a synergistic character which, when investigated further, is more obvious under harsh stress conditions induced by XA/XAO. In view that a given ROS can have detrimental effect on a particular antioxidant, it is believed that antioxidants in mixtures would provide high protection to cells or organs not only by assisting various cell defenses, but also by mutually preventing loss of their own integrity.

In conclusion, important concepts are emerging from this study: 1) cells and tissues are best protected by combination of antioxidants having a complementary spectrum of action than by any single antioxidant, 2) combinations of antioxidants can provide mutual preservation of their own integrity/activity, and 3) synergistic protection is a "latent" property of antioxidant combinations—it may be more easily detectable in particular prooxidant conditions—and occurs due to complementary antioxidant action and mutual protection.

6. References

Throughout this paper, reference is made to a number of articles of scientific literature which are listed below:

Anonymous (1985) DPD colorimetric method. Standard methods for the examination of water and wastewater. New-York, APHA, AWWA, WPCF, 16$^{th}$ ed., pp. 306–309.
Atanasiu, R., Dumoulin, M. J., Chahine, R., Mateescu, M. A. and Nadeau, R. (1995) Can. J. Physiol. Pharmacol. 73, 1253–1261.
Atanasiu, R., Gouin, L., Mateescu, M. A., Cardinal, R. and Nadeau, R. (1996) Can. J. Physiol. Pharmacol. 74, 652–656.
Atanasiu, R. L., Stéa, D., Mateescu, M. A., Vergely, C., Dalloz, F., Maupoil, V., Nadeau, R. and Rochette, L. (1998) Molec. Cell. Biochem. 189, 127–135.
Frieden, E. (1986) Clin. Physiol. Biochem. 4, 11–19.
Calabrese, L., Mateescu, M. A., Carbonaro, M. and Mondovi, B. (1988) Biochemistry International 16, 199–208.
Chahine, R., Mateescu, M. A., Roger, S., Yamaguchi, N., De Champlain, J. and Nadeau, R. (1991) Can. J. Physiol. Pharmacol. 69, 1459–1464.
Chan, P. (1996) Stroke 27, 1124–1129.
Cini, M., Fariello, R. G., Bianchetti, A. and Moretti, A. (1994) Neurochem. Res. 19, 283–288.
Chudej, L. L., Koke, J. R. and Bittar, N. (1990) Cytobios 63, 41–53.
Desagher, S., Glowinski, J. and Premont, J. (1996) J. Neurosci. 16, 2553–2562.
Di Donato, M. and Sarkar, B. (1997) Biochim. Biophys. Acta 1360, 3–16.
Dumoulin, M. J., Chahine, R., Atanasiu, R., Nadeau, R. and Mateescu, M. A. (1996) Arzneim. Forsch./Drug Res. 46, 855–861.
Erel, O. (1998) Clin. Chem. 44, 2313–2319.
Fischer, A. C. and Goode, C. A. (1994) Prep. Biochem. 24, 151–165.
Fox, P. L., Mukhopadhyay, C. and Ehrenwald, E. (1995) Life Sci. 56, 1749–1758.
Gitlin, J. D. (1998) Pediatr. Res. 44, 271–276.
Gokhale, M. S., Lin, J. R. and Yager, J. D. (1997) Toxicol. in Vitro 11, 753–759.
Halliwell, B. and Gutteridge, J. M. C. (1989) in Free Radicals in Biology and Medicine, 2nd ed., Clarendon Press, Oxford, 543 p.
Gutteridge, J. M. C. (1994) Annu. N.Y. Acad. Sci. 738, 201–213.
Gutteridge, GM and Stocks, J. (1981) Crit. Rev. Clin. Lab. Sci. 14, 257–329.
Harris, Z. L., Takahashi, Y., Miyajima, H., Serizawa, M., MacGillivray, R. T. A. and Gitlin, J. D. (1995) Proc. Natl. Acad. Sci. USA 92, 2539–2543.
Islam, K. N., Takahashi, M., Higashiyama, S., Myint, T., Uozumi, N., Kayanoki, Y., Kaneto, H., Kosaka, H. and Taniguchi, N. (1995) J. Biochem. 118, 1054–1060.
Jeannotte, R., Paquin, J., Petit-Turcotte, C. and Day, R. (1997) DNA Cell Biol. 16, 1175–1187.
Klomp, L. W., Farhangrazi, Z. S., Dugan, L. L. and Gitlin, J. D. (1996a) J. Clin. Invest. 98, 207–215.
Klomp, L. W. and Gitlin, J. D. (1996b) Hum. Mol. Genet. 5, 1989–1996.
Martin, A. (1994) U.S. Pat. No. 5,926,370.
Martin, A. (1996) Dermatol. Surg. 22, 156–160.
Mateescu, M. A., Chahine, R., Roger, S., Atanasiu, R., Yamaguchi, N., Lalumière, G. and Nadeau R. (1995) Arzneim. Forsch./Drug Res. 45, 476–480.
Mateescu, M. A., Wang, X. T., Befani, O., Dumoulin, M. J. and Mondovi, B. (1999) in Analytical and separation methods of biomacromolecules (H. Aboul-Enein, Ed.) Marcel Dekker Inc., New York, pp. 431–444.
McBurney, M. W. (1993) Int. J. Dev. Biol. 37, 135–140.
McCord J. M. (1985) N. Engl. J. Med. 312, 159–163.
Miyajima, H., Takahashi, Y., Serizawa, M., Kaneko, E. and Gitlin, J. D. (1996) Free Rad. Med. 20, 757–760.
Miyajima, H., Fujimato, M., Khono, S., Kaneko, E. and Gitlin, J. D. (1998) Neurology 51, 1188–1190.
Morita, H., Ikeda, S., Yamamoto, K., Morita, S., Yoshida, K., Nomoto, S., Kato, M. and Yanagisawa, N. (1995) Ann. Neurol. 37, 646–656.
Mukhopadhyay, C. K., Attieh, Z. K. and Fox, P. L. (1998) Science 279, 714–717.
Orena, S. J., Goode, C. A. and Linder, M. C. (1986) Biochem. Biophys. Res. Commun. 139, 822–829.
Patel, B. N. and David, S. (1997) J. Biol. Chem. 272, 20185–20190.
Peuchen, S., Bolanos, J. P., Heales, S. J., Almeida, A., Duchen, M. R. and Clark, J. B. (1997) Prog. Neurobiol. 52, 261–281.
Shah, A. B., Chernov, I., Zhang, H. T., Ross, B. M., Das, K., Lutsenko, S., Parano, E., Pavone, L., Evgrafov, O., Ivanova-Smolenskaya, I. A., Anneren, G., Westermark, K., Urrutia, F. H., Penchaszadeh, G. K., Sternlieb, I., Scheinberg, I. H., Gilliam, T. C. and Petrukhin, K. (1997) Am. J. Hum. Genet. 61, 317–328.
Sheridan, J., Kern, E., Martin, A. and Booth, A. (1997) Antiviral Res. 36, 157–166.
Stevens, M. O., DiSilvestro, R. A. and Harris, E. D. (1984) Biochemistry 23, 261–266.
Takemura, G., Onodera, T. and Ashraf, M. (1994) J. Mol. Cell Cardiol. 26, 441–454.
Vaughan W. (1991) Circulation 84, 1831–1851.
Walker, M. J., Curtis, M. J., Hearse, D. J., Campbell, R. W., Janse, M. J., Yellon, D. M., Cobbe, S. M., Coker, S. J., Harness, J. B., Harron, D. W., Northover, B. J., Parratt, J. R., Riemersma, R. A., Riva, E., Russell, D.C., Sheridan, D. J., Winslow, E. and Woodward, B. (1988) Cardiovasc. Res. 22, 447–455.

Wang, R., Zhang, L., Mateescu, M. A. and Nadeau, R. (1995) Biochem. Biophys. Res. Commun. 207, 599–606.

Wang, X. T., Dumoulin, M. J., Befani, O., Mondovi, B. and Mateescu, M. A. (1994) Preparative Biochemistry 24, 237–250.

Yao, M., Bain, G. and Gottlieb, D. I. (1995) J. Neurosci. Res. 41, 792–804.

Of course, numerous modifications and improvements could be made to the embodiments that have been disclosed herein above. These modifications and improvements should, therefore, be considered a part of the invention.

What is claimed is:

1. A neuroprotective composition comprising:
   (a) ceruloplasmin; and
   (b) a mixture of pyruvate, at least one antioxidant, and at least one lipid.

2. The neuroprotective composition of claim 1, wherein said at least one lipid consists of at least one fatty acid selected from the group consisting of monoglycerides, diglycerides, triglycerides, free fatty acids, and mixtures thereof.

3. The neuroprotective composition of claim 2, characterized in that said at least one fatty acid consists of a mixture of saturated and unsaturated fatty acids.

4. The neuroprotective composition of claim 3, characterized in that said fatty acids are present in an amount varying from about 0.001% v/v to about 1% v/v, by weight of the neuroprotective composition.

5. The neuroprotective composition of claim 1, wherein the pyruvate is selected from the group consisting of pyruvic acid, pharmaceutically acceptable salts of pyruvic acid, and mixtures thereof.

6. The neuroprotective composition of claim 5, wherein pyruvate is present in said composition in an amount varying from about 0.01 mM to about 100 mM.

7. The neuroprotective composition of claim 1, wherein said at least one antioxidant is selected from the group consisting of Vitamin A, carotene, Vitamin E, pharmaceutically acceptable salts thereof, and mixtures thereof.

8. The neuroprotective composition of claim 1, wherein said at least one antioxidant is selected from the group consisting of Vitamin E, Vitamin E acetate and analogues of Vitamin E.

9. The neuroprotective composition of 1, wherein said at least one antioxidant is present in an amount varying from about 0.01 unit/ml to about 10 unit/ml of said composition.

10. The neuroprotective composition of claim 1, wherein it further comprises an agent selected from the group consisting of metal chelataors, metal scavengers, proteinic metal chelators, proteinic metal scavengers, preserving agents, solublizing agents, stabilizing agents, wetting agents, emulsifiers, sweeteners, colorants, odorants, salts, buffers, and coating agents.

11. A method for treating a neuronal oxidative stress related condition or for protecting neuronal cells against an oxidative stress, comprising the administration to a patient in need thereof of a therapeutically effective amount of a neuroprotective composition comprising:
   i) ceruloplasmin and
   ii) a mixture of pyruvate, at least one antioxidant, and at least one lipid.

12. A method for preparing a neuroprotective composition, comprising the steps of:
   a) providing a therapeutically effective amount of i) ceruloplasmin, ii) pyruvate, iii) at least one antioxidant and iv) at least one lipid; and
   b) mixing together components i), ii), iii) and iv) of step a) in a buffered saline solution to obtain a pharmaceutically acceptable homologous suspension.

* * * * *

UNITED STATES PATENT AND TRADEMARK OFFICE
CERTIFICATE OF CORRECTION

PATENT NO. : 6,780,842 B2 Page 1 of 1
DATED : August 24, 2004
INVENTOR(S) : Joanne Paquin, Mircea-Alexandru Mateescu and Eric DeGranpre It is certified that error appears in the above-identified patent and that said Letters Patent is hereby corrected as shown below:

Column 26,
Line 9, insert -- claim -- after "neuroprotective composition of" and before "1".
Line 14, insert -- chelators -- instead of "chelataors"

Signed and Sealed this

Seventh Day of December, 2004

JON W. DUDAS
*Director of the United States Patent and Trademark Office*